(12) United States Patent
Levon et al.

(10) Patent No.: US 7,462,512 B2
(45) Date of Patent: Dec. 9, 2008

(54) FLOATING GATE FIELD EFFECT TRANSISTORS FOR CHEMICAL AND/OR BIOLOGICAL SENSING

(75) Inventors: Kalle Levon, Brooklyn, NY (US);
Arifur Rahman, San Jose, CA (US);
Tsunehiro Sai, New York, NY (US);
Ben Zhao, Brooklyn, NY (US)

(73) Assignee: Polytechnic University, Brooklyn, NY (US)

( * ) Notice: Subject to any disclaimer, the term of this patent is extended or adjusted under 35 U.S.C. 154(b) by 445 days.

(21) Appl. No.: 11/033,046

(22) Filed: Jan. 11, 2005

(65) Prior Publication Data
US 2005/0230271 A1   Oct. 20, 2005

Related U.S. Application Data

(60) Provisional application No. 60/535,975, filed on Jan. 12, 2004.

(51) Int. Cl.
*H01L 21/00* (2006.01)
(52) U.S. Cl. .................. 438/123; 257/414; 438/48; 438/49; 438/56; 438/257
(58) Field of Classification Search ............ 438/48, 438/49, 56, 257; 257/253, 414
See application file for complete search history.

(56) References Cited

OTHER PUBLICATIONS

Bausells et al. "Ion-sensitive transistors fabricated in a commercial CMOS technology", Sensors and Actuators B vol. 57, (1999) pp. 56-62.*
Janata, J. "Potentiometric Microsensors", Chemical Reviews vol. 90 (1990) pp. 691-703.*

* cited by examiner

*Primary Examiner*—Carl Whitehead, Jr.
*Assistant Examiner*—Sonya D McCall
(74) *Attorney, Agent, or Firm*—Straub & Pokotylo; John C. Pokotylo

(57) ABSTRACT

Specific ionic interactions with a sensing material that is electrically coupled with the floating gate of a floating gate-based ion sensitive field effect transistor (FGISFET) may be used to sense a target material. For example, an FGISFET can use (e.g., previously demonstrated) ionic interaction-based sensing techniques with the floating gate of floating gate field effect transistors. The floating gate can serves as a probe and an interface to convert chemical and/or biological signals to electrical signals, which can be measured by monitoring the change in the device's threshold voltage, $V_T$.

7 Claims, 17 Drawing Sheets

US 7,462,512 B2

FLOATING GATE FIELD EFFECT TRANSISTORS FOR CHEMICAL AND/OR BIOLOGICAL SENSING

§ 0. RELATED APPLICATIONS

This application claims benefit to U.S. Provisional Application Ser. No. 60/535,975, titled "A CMOS-COMPATIBLE ION SENSITIVE FIELD EFFECT TRANSISTOR (ISFET) FOR CHEMICAL AND BIOLOGICAL SENSING" filed on Jan. 12, 2004 and listing Kalle Levon, Ben Zhao, Tsunehiro Sai, and Arifur Rahman as inventors (referred to as "the '975 provisional"). That application is incorporated herein by reference. The scope of the present invention is not limited to any requirements of the specific embodiments described in that application.

§ 1. BACKGROUND

§ 1.1 Field of the Invention

The present invention concerns biological and/or chemical sensing. In particular, the present invention concerns floating gate (e.g., silicon or organic) transistors, such as Ion Sensitive Field Effect Transistors (ISFETs) for example, for chemical and/or biological sensing.

§ 1.2 Background Information

The key element of a conventional silicon-based ISFET is a gate capacitor formed between the gate and substrate. The electric field within the gate (or oxide) capacitor is determined by the difference in work function of the plate materials forming the gate and silicon substrate. The electric field within the gate oxide determines the amount of surface charge near the silicon and oxide interface and sets the conductivity of the field effect transistor (FET) (between source and drain).

If the gate of an ISFET is formed by a material which is sensitive to selective gases or analytes, the electric field within gate oxide will be determined by the electrochemical properties of the combined (gate and gas or analyte) system. This mechanism has been exploited to design various types of silicon based ISFETs. (See, e.g., C. G. Jakobson, U. Dinnar, M. Feinsod, and Y. Nemirovsky, "Ion-Sensitive Field-Effect Transistors in Standard CMOS Fabrication by Post Processing," *IEEE Sensors Journal*, (2002); and J. Janata, "Electrochemical Microsensors," *Proceedings of the IEEE*, Vol. 91(6), pages 864-869 (2003), both incorporated herein by reference.)

FIG. 1 depicts a conventional ion sensitive field effect transistor (ISFET) submerged in gas or analyte. Specifically, silicon based ISFET 120 comprising a gate 130, a source 124, a drain 126, a silicon oxide layer 128, and a silicon substrate 122 is exposed to a sample (gas or analyte) in a container 110 with a reference electrode 140 so as to detect the presence and/or amount or concentration of a target in the sample.

Although conventional Si-based ISFETs can sense various types of targets, there are some limitations that prevent their widespread deployment. For example, in a conventional scheme for ISFET-based sensing, such as that shown in FIG. 1, the gate 130 voltage is set by the electrochemical properties of the sensing material and the bias voltage of a reference electrode 140. Due to this reference electrode-based biasing scheme, these ISFETs are suitable as pH sensors, but they have limited use as gas sensors.

To overcome some of these limitations, the electrical properties of the conductive channel of ISFETs can be modulated directly, without the intervention of gate electrode, as shown in FIG. 2. FIG. 2 depicts a conducting polymer-based ISFET 210 exposed to gas or analyte. Specifically, an organic-based ISFET 210 comprises a gate 220, a source 214, a drain 216, an oxide layer 218, and a conducting polymer substrate 212 (which includes conductive channel from source 214 to drain 216). This ISFET 210 may be exposed to a sample (gas or analyte) so as to detect the presence and/or amount or concentration of a target in the sample. Although the use of conducting polymer-based ISFETs simplifies the sensing measurements, only those ISFETs having a conducting polymer as the channel/substrate material have shown promising results. Unfortunately, organic FETs generally have a much lower drive current compared to bulk silicon devices. Consequently, a comparatively large (e.g., high device width/length ratio) device is required for acceptable drive current to suppress the affect of background noise and to minimize the need for significant amplification of the detected signal. It is also difficult to integrate on-chip bias and peripheral circuits with organic FETs, and they are not as easily miniaturizable as silicon FETs.

In view of the foregoing disadvantages of known transistor-based sensors, it would be useful to provide improved sensors which overcome one or more of such disadvantages.

§ 2. SUMMARY OF THE INVENTION

Embodiments consistent with the present invention can leverage specific ionic interactions with a sensing material that is electrically coupled with the floating gate of a floating gate ion sensitive field effect transistor (FGISFET) to sense a target material. For example, an FGISFET can use (e.g., previously demonstrated) ionic interaction-based sensing techniques with the floating gate of double gate (i.e., floating gate and control gate) field effect transistors. The floating gate serves as a probe and an interface to convert chemical and/or biological signals to electrical signals, which can be measured by monitoring the change in the device's threshold voltage, $V_T$.

§ 3. BRIEF DESCRIPTION OF THE DRAWINGS

Figure 11:
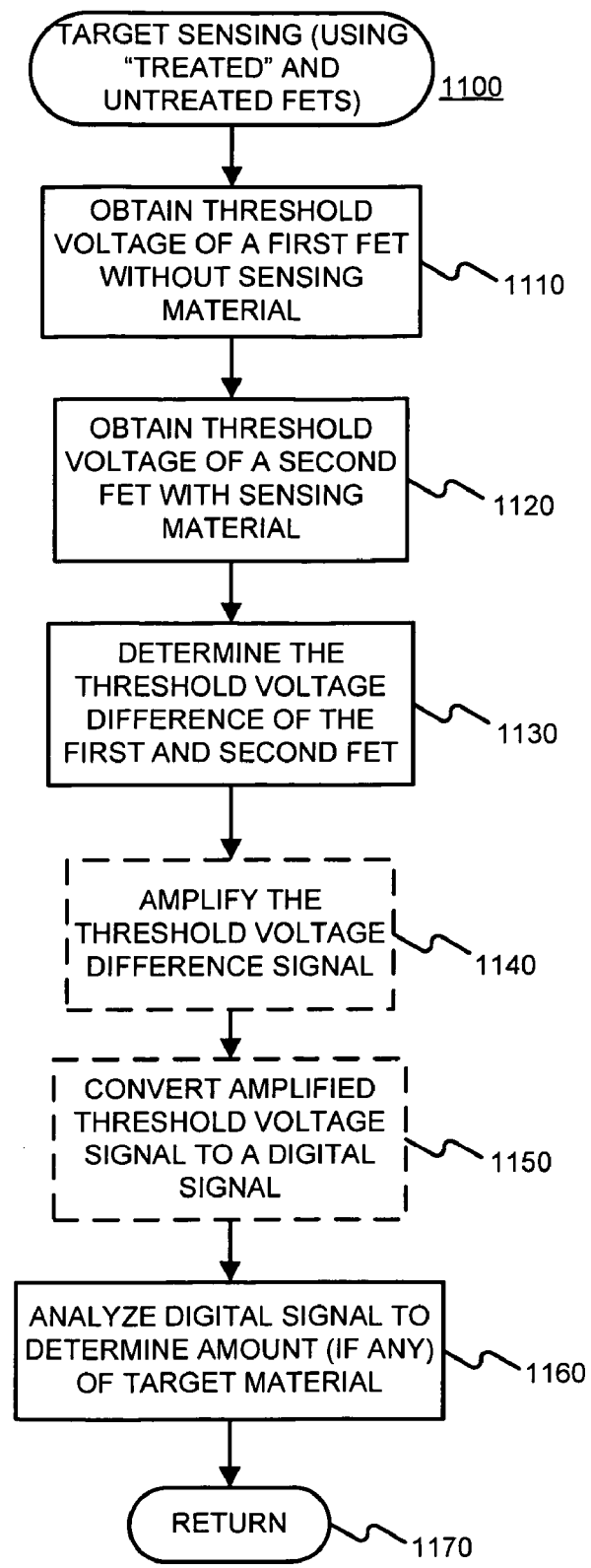

FIG. 11 flow diagram of an exemplary method that may be used to determine the presence, amount, and/or concentration of a target material using a double ISFET sensor with a differential amplifier based read-out circuit in a manner consistent with the present invention.

Figure 12:
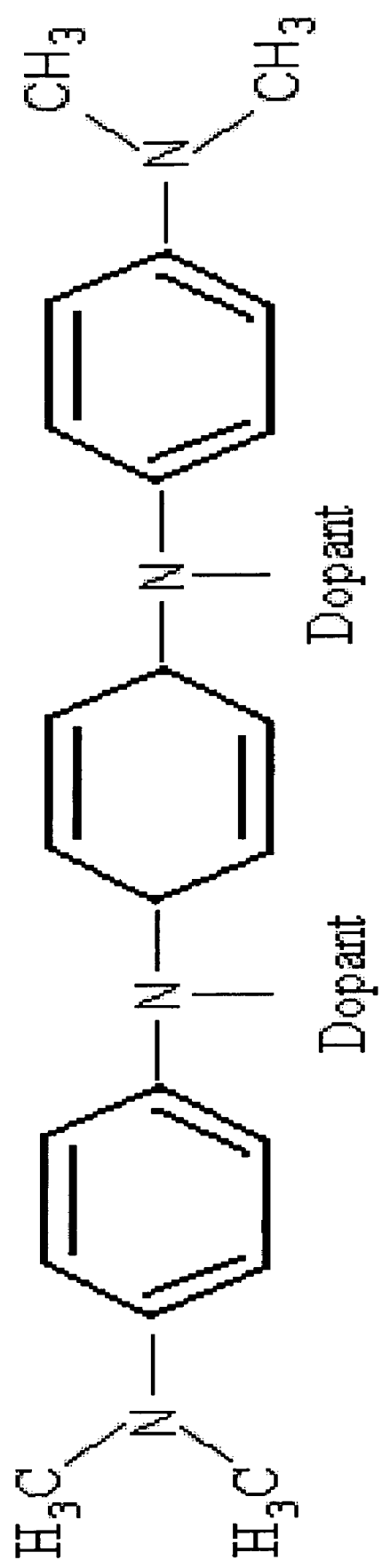

FIG. 12 depicts the chemical structure of an aniline trimer used as a sensing material in an exemplary embodiment consistent with the present invention.

Figure 13:
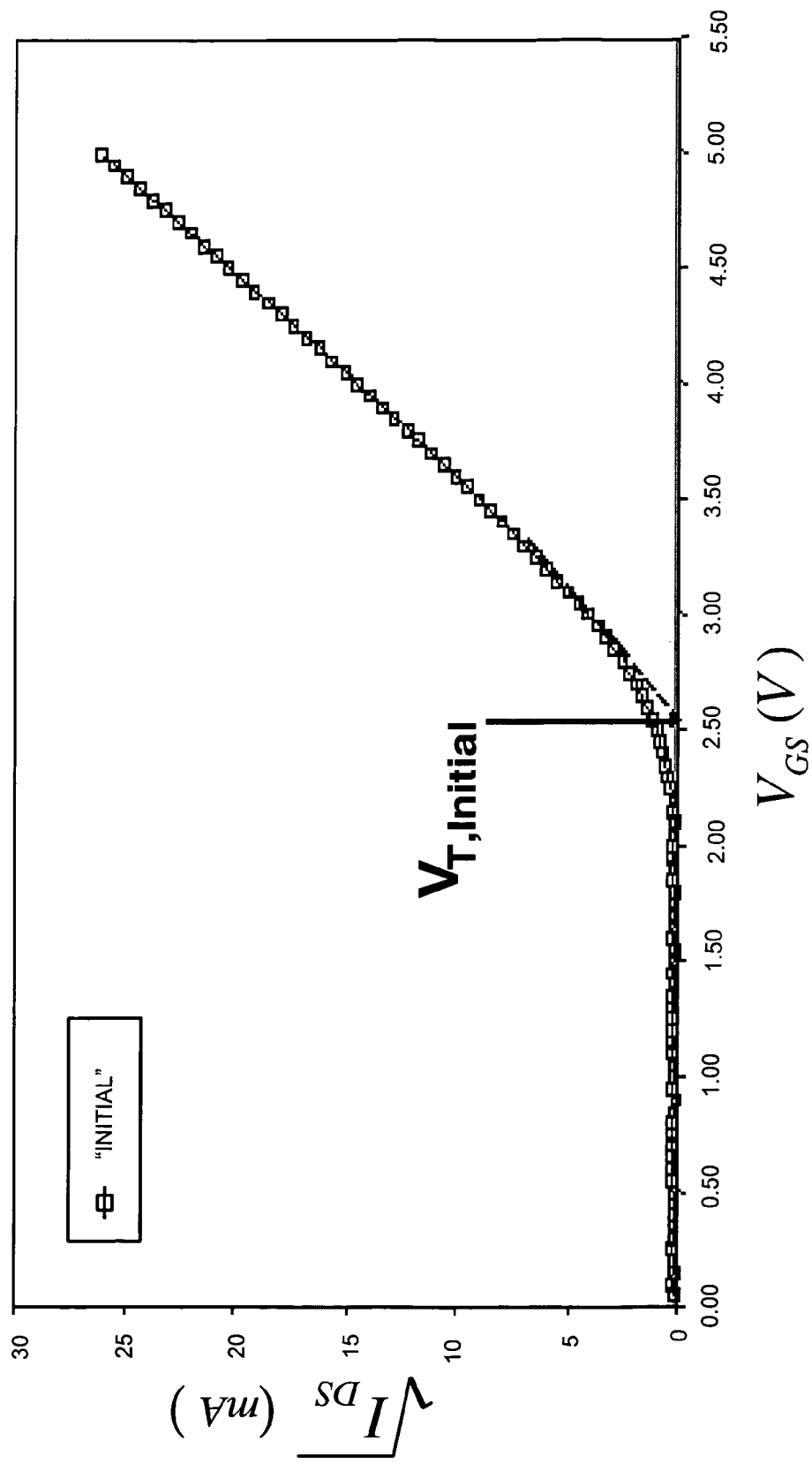

FIG. 13 is a chart depicting $\sqrt{I_{DS}}$ versus $V_{GS}$ characteristics of an exemplary FGISFET biased in saturation region, and indicating the initial threshold voltage.

Figure 14:
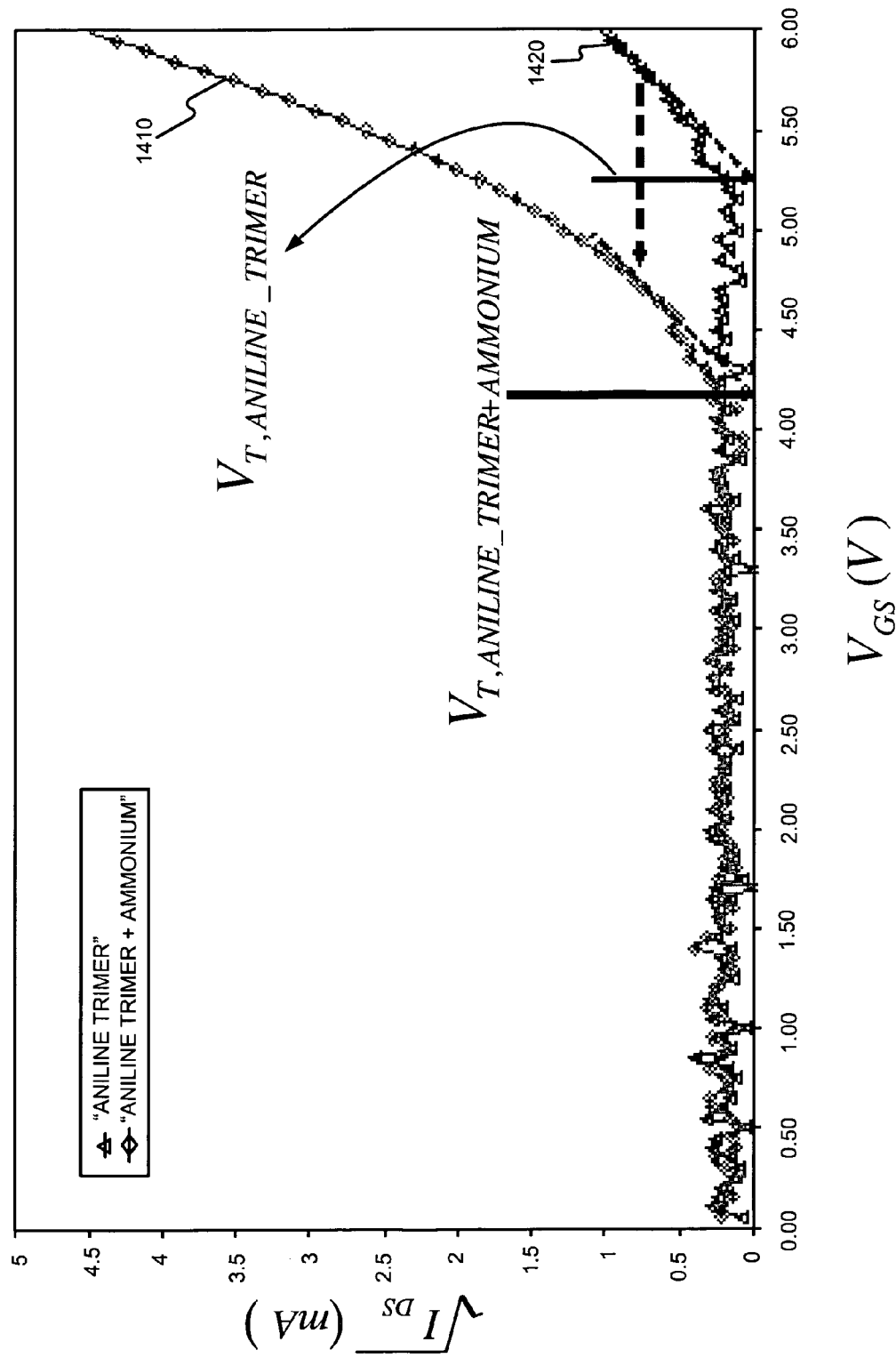

FIG. 14 is a chart depicting $\sqrt{I_{DS}}$ versus $V_{GS}$ characteristics of an exemplary FGISFET with an aniline trimer as a sensing material and the FGISFET with an aniline trimer as a sensing material exposed to ammonium, along with the indicated threshold voltages.

Figure 15:
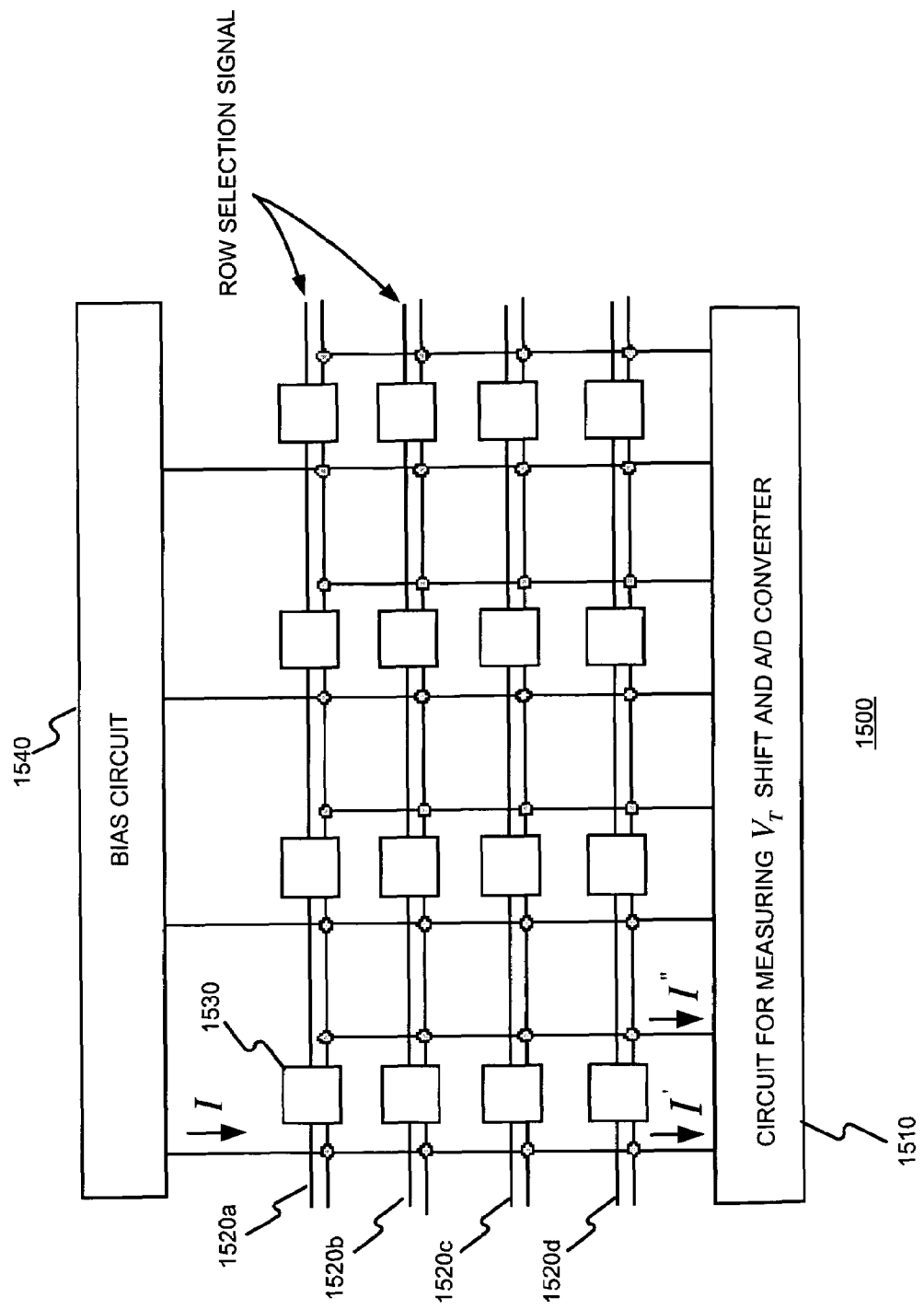

FIG. 15 illustrates an array of FGISFETs with peripheral circuitry that may be used for detecting multiple targets and/or minimizing errors.

Figure 16:
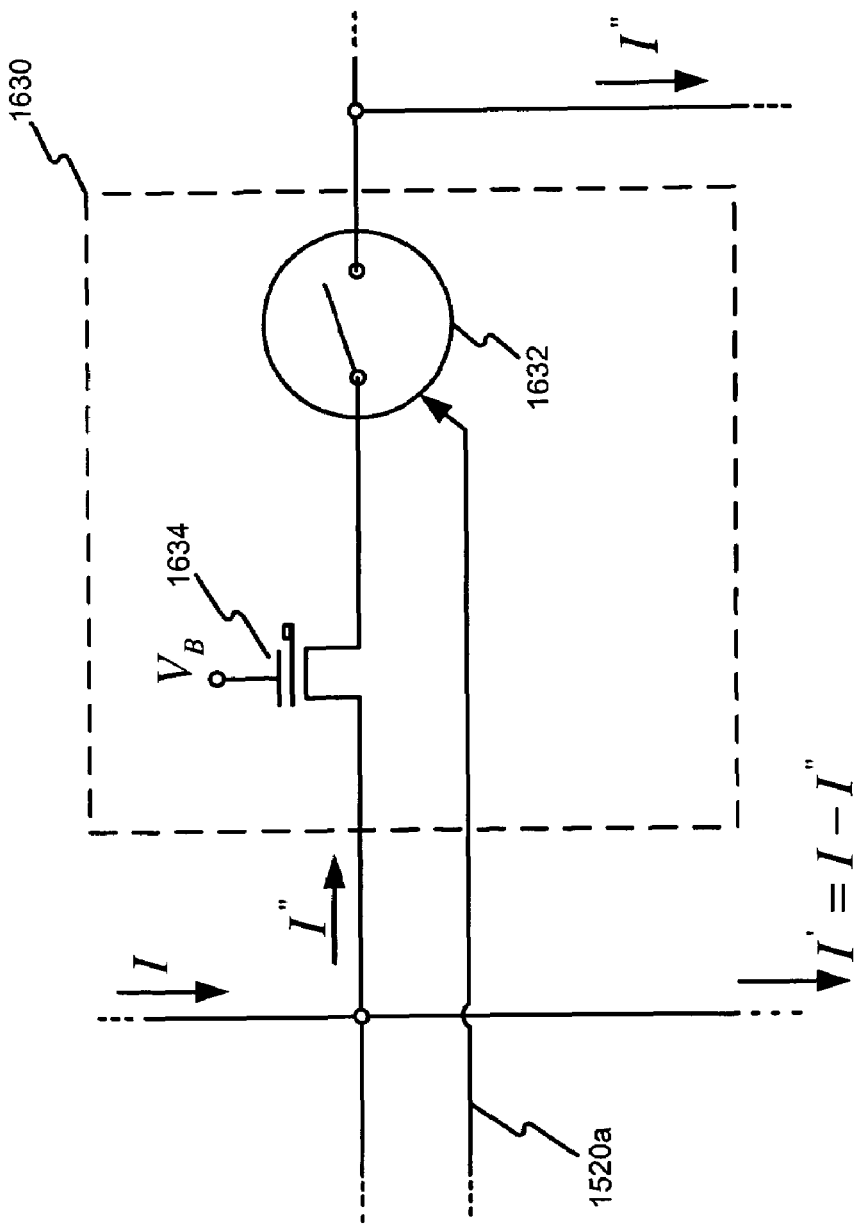

FIG. 16 illustrates a schematic diagram of an exemplary ISFET element consistent with the present invention, which may be used in an array such as the one depicted in FIG. 15.

Figure 17:
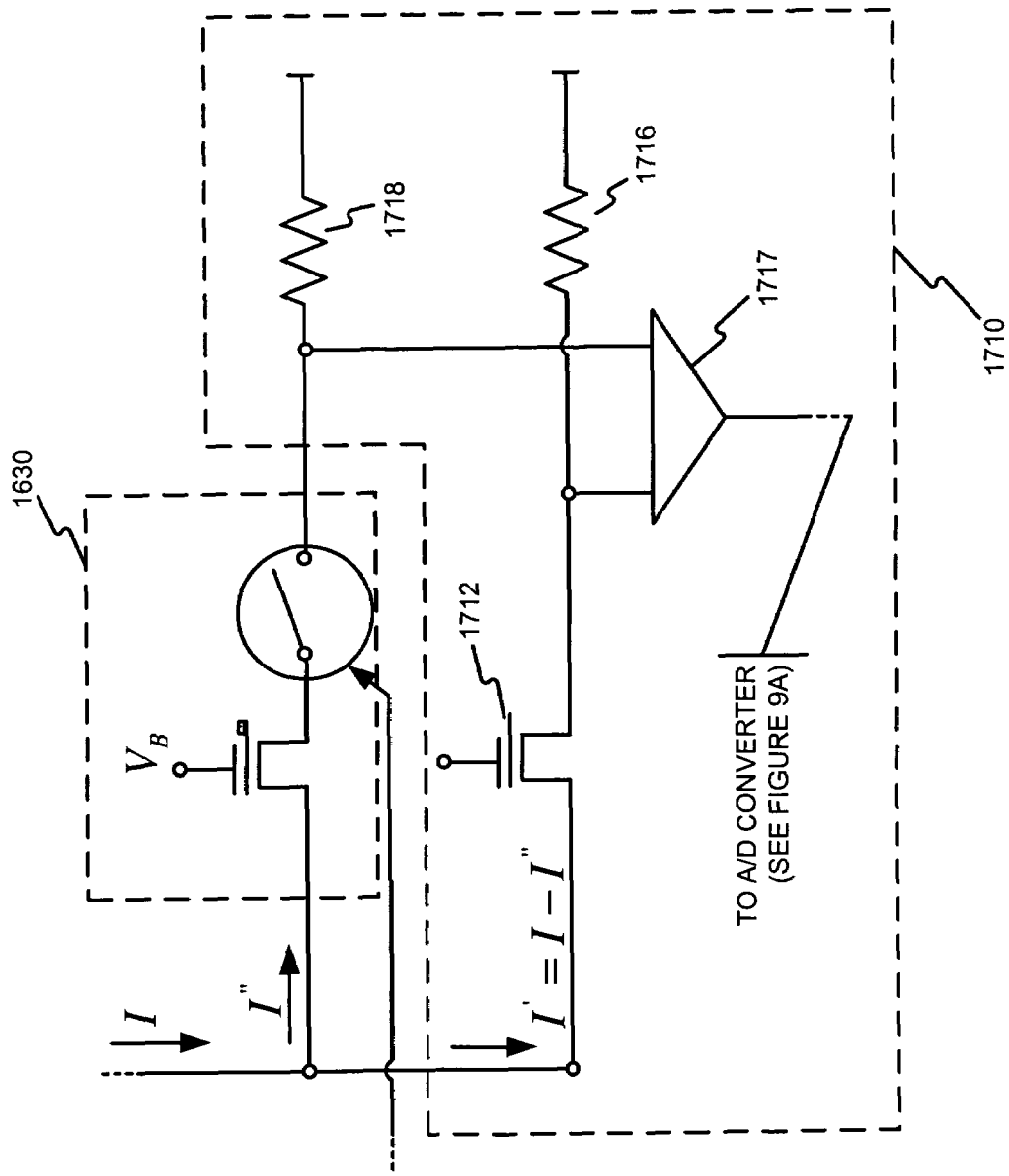

FIG. 17 illustrates a schematic diagram of exemplary shift measurement circuitry, consistent with the present invention, which may be used in an array such as the one depicted in FIG. 15.

§ 4. DETAILED DESCRIPTION

The present invention may involve novel methods, apparatus, compositions of matter, and combinations for chemical and/or biological sensing using a floating gate (e.g., ion sensitive) field effect transistor. The following description is presented to enable one skilled in the art to make and use the invention, and is provided in the context of particular applications and their requirements. Thus, the following description of embodiments consistent with the present invention provides illustration and description, but is not intended to be exhaustive or to limit the present invention to the precise form disclosed. Various modifications to the disclosed embodiments will be apparent to those skilled in the art, and the general principles set forth below may be applied to other embodiments and applications. For example, although a series of acts may be described with reference to a flow diagram, the order of acts may differ in other implementations when the performance of one act is not dependent on the completion of another act. Further, non-dependent acts may be performed in parallel. As another example, different sensing materials or types of sensing materials may be used, in electrically conductive connection with a floating gate electrode, to sense different targets or types of targets. No element, act or instruction used in the description should be construed as critical or essential to the present invention unless explicitly described as such. Also, as used herein, the article "a" is intended to include one or more items. Where only one item is intended, the term "one" or similar language is used. Thus, the present invention is not intended to be limited to the embodiments shown and the inventors regard their invention as any patentable subject matter described.

§ 4.1 FIRST EMBODIMENT

Figure 1:
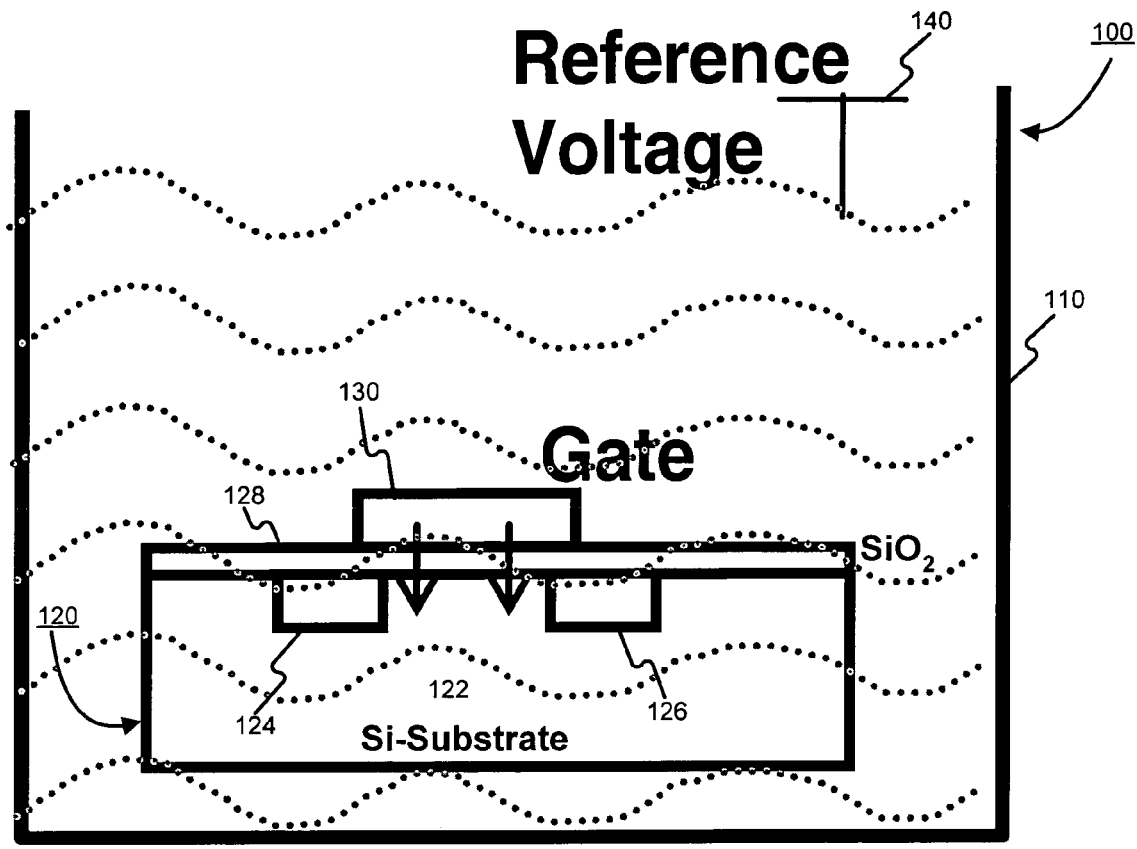
FIG. 1 depicts a conventional ion sensitive field effect transistor (ISFET) submerged in gas or analyte.
Figure 2:
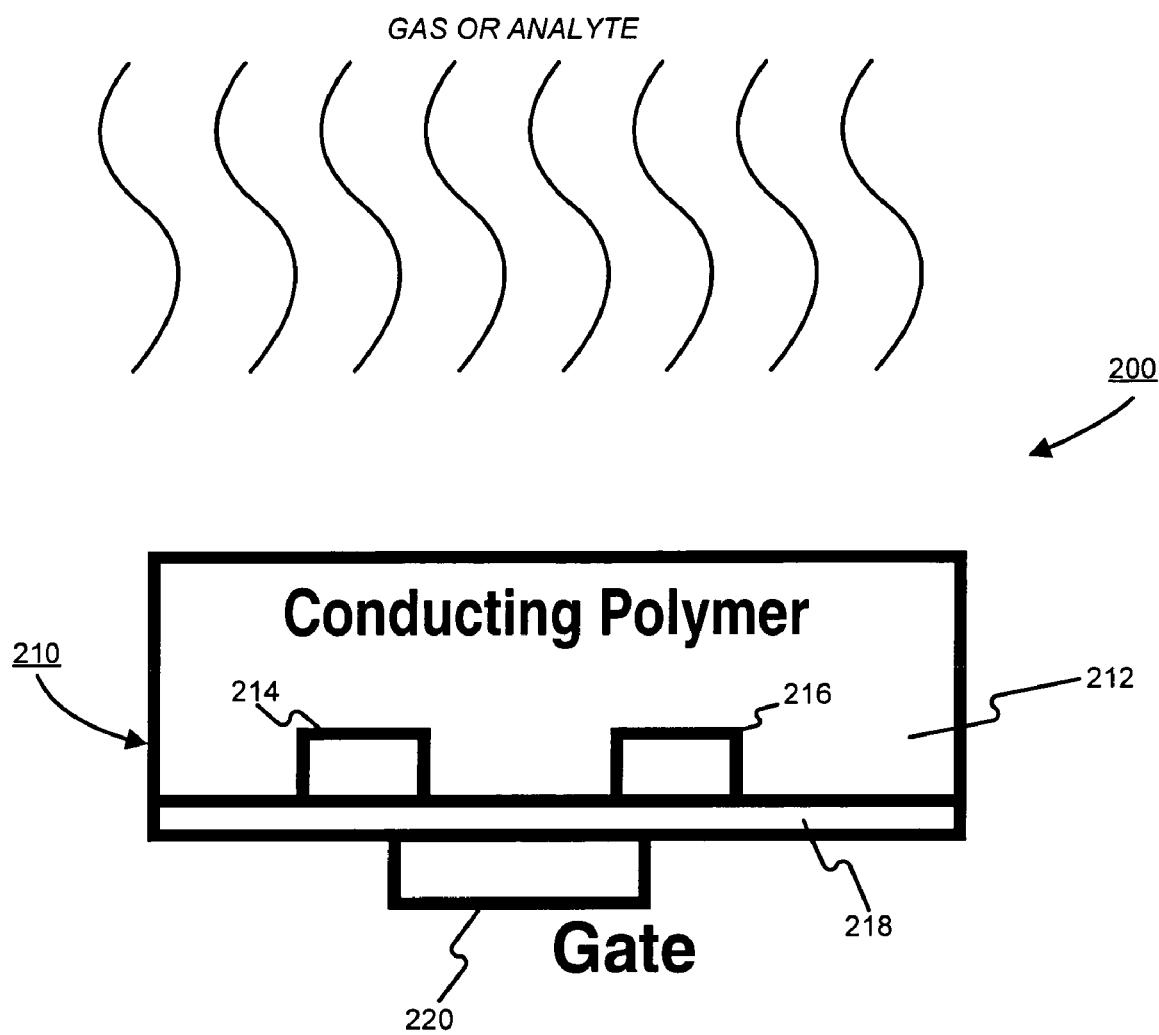
FIG. 2 depicts a conventional conducting polymer-based ISFET exposed to gas or analyte.
Figure 3:
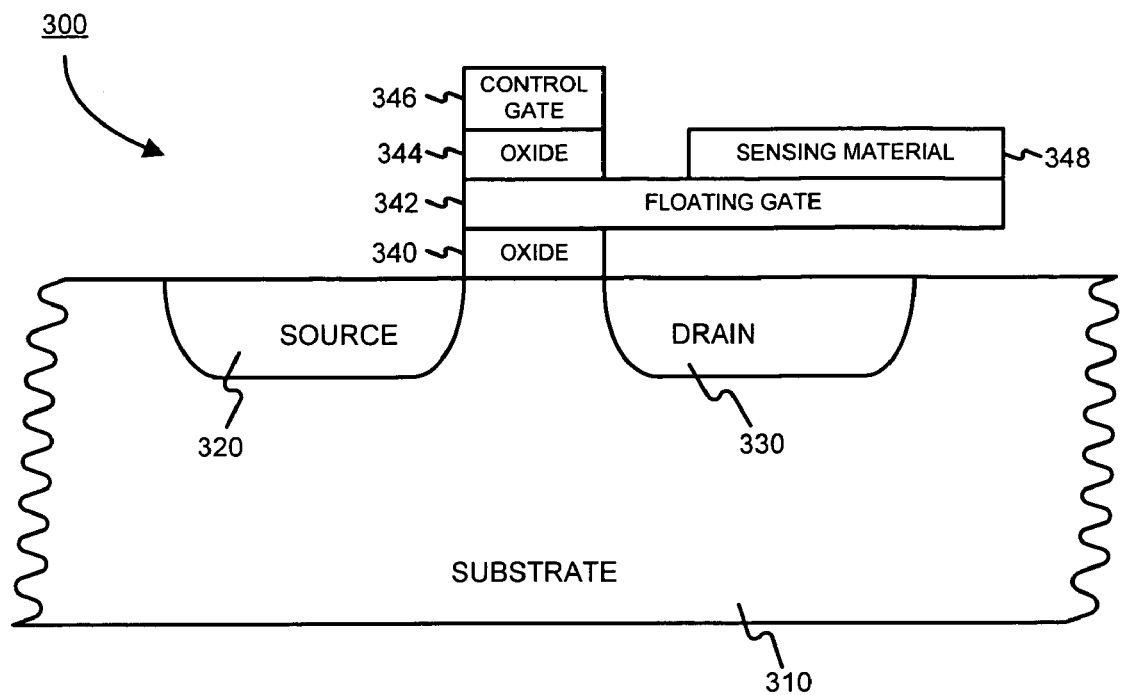
FIG. 3 illustrates a cross sectional view of an exemplary floating gate ion sensitive field effect transistor (FGISFET) that is consistent with the present invention.

FIG. 3 illustrates a cross sectional view of an exemplary floating gate ion sensitive field effect transistor 300 (FGISFET), consistent with the present invention, that overcomes at least some of the limitations of conventional and organic ISFETs introduced in § 1.2 above. The exemplary FGISFET 300 may comprise a substrate 310 (which may be silicon-based or organic, for example, though is preferably not organic), a source 320, a drain 330, a first insulating layer (e.g., an oxide layer) 340, a floating gate 342, a second insulating layer (e.g., an oxide layer) 344, a sensing material 348 and a control gate 346. The control gate 346 may be used for setting the sensor's operating point and the floating gate 342 may be used to measure ionic activity associated with a target material. The sensing material 348 may be an ion-sensitive material that may be selected to sense a specific chemical, a specific class of chemicals, a specific biological material, and/or a specific class of biological materials. Although the sensing material 348 is shown as being arranged on (e.g., deposited on) the floating gate 342, it may be arranged on some other conductive surface which is electrically coupled with the floating gate 342.

The device structure may be similar to that of a floating gate FET which is widely used for EPROM or Flash memory. (See, e.g., S. M. Kang and Y. Leblebici, *CMOS Digital Integrated Circuits*, Third Edition, McGraw Hill (2002), incorporated herein by reference.) In a floating gate FET, threshold voltage (i.e., the gate voltage required to induce minority carriers at the oxide-silicon interface) is determined by the difference in work function between the floating gate 342 and substrate 310 and the amount of charges injected or trapped on the floating gate 342. The sensing material 348 may be an ion-sensitive material and may modify the threshold voltage. The threshold voltage can be modified (i) after the application of sensing material, such as polyanaline, on floating gate due to its ionic charge (referred to as "doping") characteristics; (ii) during the sensing process due to the binding (or some other interaction) of target material (such as ammonia) with sensing material and the de-doping of sensing material; and/or (iii) during the sensing process due to the binding (or some other interaction) of target material with sensing material and consequent change of ionic charge of the sensing material, etc.

Unlike conventional silicon-based ISFETs, the control gate 346 voltage can be set directly to a desired value for optimum sensitivity and dynamic range. The FGISFETs are suitable for sensing analytes, gases, etc. In addition, the FGISFET can be miniaturized, and integrated with on-chip bias, read out, and/or signal processing circuits. The exemplary FGISFET may also benefit from technology scaling that has revolutionized the semiconductor industry. Potentially, millions of such FGISFETs can be fabricated on a single chip and structured in a way similar to an array of complementary field effect transistor (CMOS) or charge coupled device (CCD) based image sensors, which are commonly used in digital cameras. Thus, the FGISFET can provide a basis for low-cost, miniaturizable and portable solutions to chemical and/or biological sensors.

Thus, embodiments consistent with the present invention can leverage specific ionic interactions with a sensing material 348 electrically coupled with the floating gate 342 of a floating gate based ion sensitive field effect transistors (FGISFET) 300 to sense a target material. In recent work on chemical sensors, a surface imprinting method has been developed, which creates cavities on the ion sensitive electrode (Indium Tin Oxide (ITO)). This method has been applied for sensing various chemical agents. In parallel, research on biological sensors have screened a vast variety of ligands, which interact with bacterial spores and created a library of these specific ionic ligands, which include antibodies, aptamers, lectins, heptapeptides and sugars, and also synthetic ionic molecules (See, e.g., K. Levon, B. Yu, "Development of Multivalent Macromolecular Ligands for Enhanced Detection of Biological Targets," submitted to IUPAC PC Symposium Series and the utility and provisional patent applications listed in § 4.4 below.)

The exemplary FGISFET 300 can use (e.g., previously demonstrated) ionic interaction-based sensing techniques with the floating gate of double gate (i.e., floating gate and control gate) field effect transistors. The floating gate serves as a probe and an interface to convert chemical and/or biological signals to electrical signals, which can be measured by monitoring the change in the device's threshold voltage, $V_T$.

§ 4.1.1 FET Design

Figure 4:
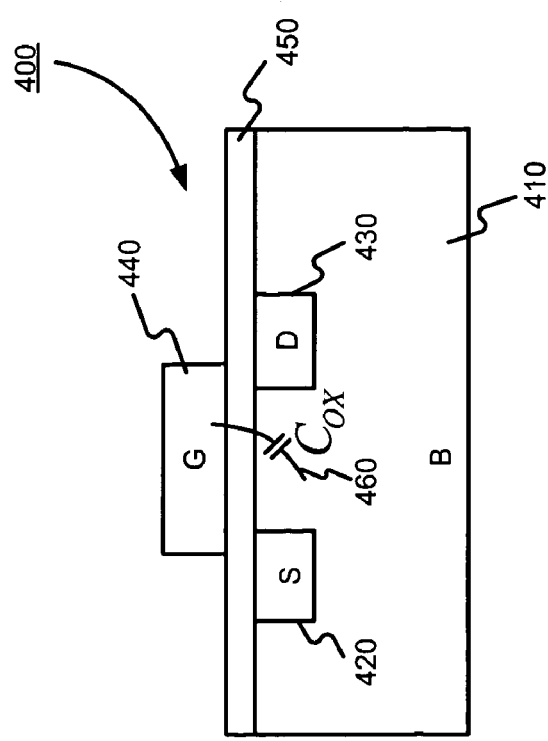
FIG. 4 illustrates a cross sectional view of a conventional field effect transistor.

FIG. 4 illustrates a cross sectional view of a conventional field effect transistor 400. A typical field effect transistor 400, as shown in FIG. 4 is a four terminal device, fabricated in either n-type or p-type silicon substrate (B) 410. These four terminals are source (S) 420, drain (D) 430, gate (G) 440, and bulk/substrate (B) 410. An insulating layer (e.g., an oxide layer) 450 is arranged between the gate and the substrate 410. The gate oxide capacitance per unit area is depicted with 460 and does not imply a physical capacitor as part of a FET.

The gate 440 electrode controls the amount of charges flowing between source 420 and drain 430. In the case of an n-type FET (nFET), if the voltage difference between gate 440 and source 420 ($V_{GS}$) is higher than a threshold voltage ($V_T$), a conductive channel is formed in the substrate 410 between source 420 and drain 430. By applying a positive drain-to-source voltage ($V_{DS}$), current flow is established between drain 430 and source 420 terminals. The conductivity of the channel (or drain current) is controlled by gate-to-source and drain-to-source voltages, as well as material properties and dimensions of the substrate 410 and gate electrode 440.

The threshold voltage of a field effect transistor is determined by the difference in work function between the gate electrode 440 and silicon substrate 410, material and physical properties of the oxide layer 450 located between the gate electrode 440 and channel (substrate region 410 between the source 420 and drain 430), and the interfacial characteristics of gate oxide. The threshold voltage of a single-gate field effect transistor ($V_T^{SG}$) is given by:

$$V_T^{SG} = \Phi_{GC} - 2\phi_F - \frac{Q_B}{C_{OX}} - \frac{Q_{OX}}{C_{OX}}$$

where $\Phi_{GC}$ is the difference in work function between gate 440 and channel, $2_{\phi F}$ is substrate Fermi potential, $Q_B$ is the depletion region charge density, $Q_{OX}$ is Si—SiO$_2$ interface charge density, and $C_{OX}$ is the gate oxide capacitance per unit area.

Figure 5:
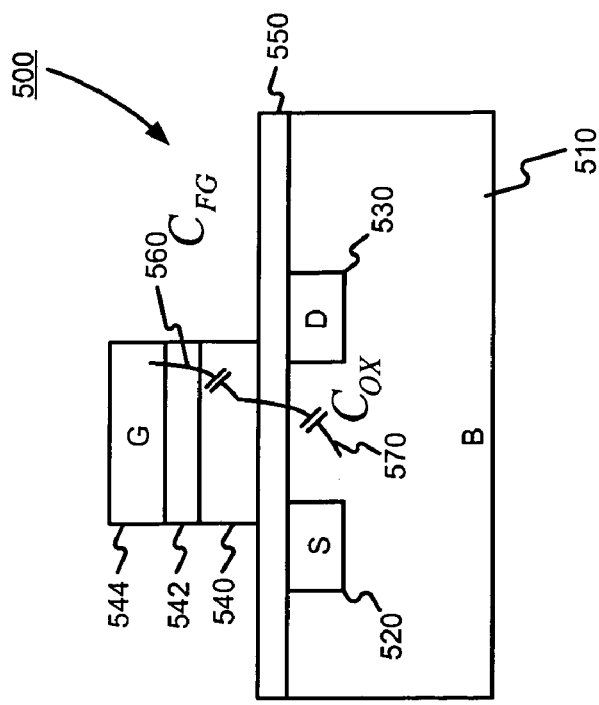
FIG. 5 illustrates a cross sectional view of a conventional floating gate field effect transistor.

FIG. 5 illustrates a cross sectional view of a conventional floating gate field effect transistor 500. The floating gate FET 500 in general has many commonalities to a regular FET and its operation is similar to a regular FET. Specifically, the floating gate FET 500 may comprise a substrate (B) 510, a source (S) 520, a drain (D) 530, an insulating layer (e.g., an oxide layer) 550, a floating gate (e.g., highly doped polysilicon) 540, another insulating layer (e.g., a second oxide layer) 542, and a control gate (G) (e.g., highly doped polysilicon) 544. The floating gate-oxide capacitance per unit area is depicted by element 570, and the capacitance per unit area between the control gate and floating gate is depicted by element 560. Note that elements 560 and 570 do not imply physical capacitors as part of a floating gate FET.

The threshold voltage $V_T^{FG}$ of the FGFET 500 is given by:

$$V_T^{FG} = \frac{C_{OX} + C_{FG}}{C_{FG}} V_T^{SG} - \frac{Q_{FG}}{C_{FG}}$$

where $C_{FG}$ is the capacitance per unit area between the control and floating gates, $Q_{FG}$ is the net charge on floating gate 540.

If ion-sensitive sensing material is applied to the floating gate 540, as a result of its ionic response to specific targets, there is a net change in the value of $Q_{FG}$. This net change can be determined by measuring the shift in $V_T^{FG}$. In other words, the shift in $V_T^{FG}$ is directly related to the detection of a specific target. Further, the extent of the $V_T^{FG}$-shift may be related to the amount, strength, and/or concentration of the target. In the saturation region of operation of a long channel MOSFET, the drain current is given by:

$$I_{DS} = \frac{\mu C_{OX}}{2} \frac{W}{L} (V_{GS} - V_T)^2$$

where $\mu$ is the mobility of the carriers, and W/L is the width/length ratio of the field effect transistor. By plotting $\sqrt{I_{DS}}$ versus $V_{GS}$, the x-axis intercept, $V_T$, can be determined. There are also other sophisticated techniques that can be used to estimate the value of threshold voltage. (See, e.g., K. Terada, K. Nishiyama, K. I. Hatanaka, "Comparison of MOSFET-threshold voltage extraction methods," *Solid State Electronics*, vol. 45, pages 35-40 (2001), incorporated herein by reference.)

§ 4.1.2 FET Fabrication

Figure 7A:
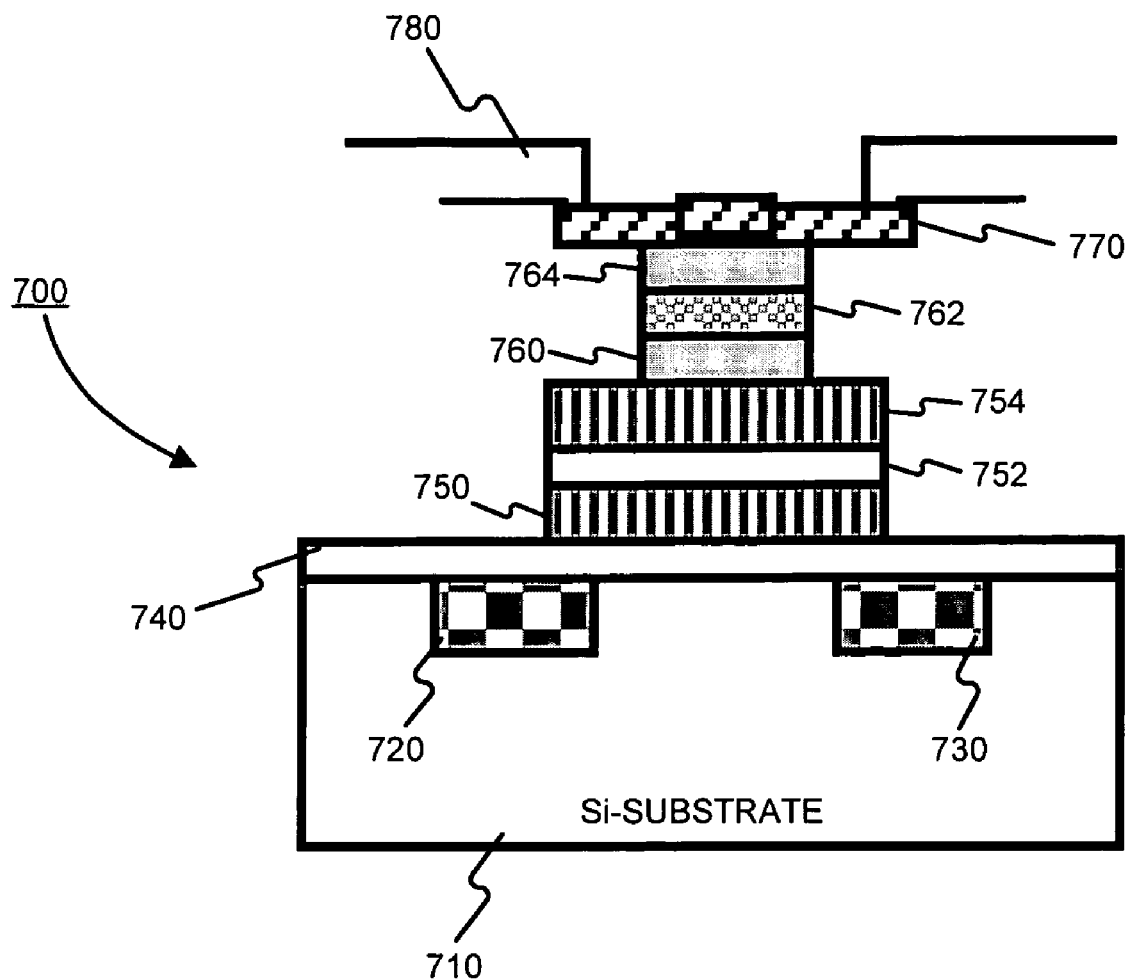
FIGS. 7A and 7B illustrate a cross sectional front view and a plan view, respectively, of an exemplary floating gate ion sensitive field effect transistor that is consistent with the present invention.
Figure 7B:
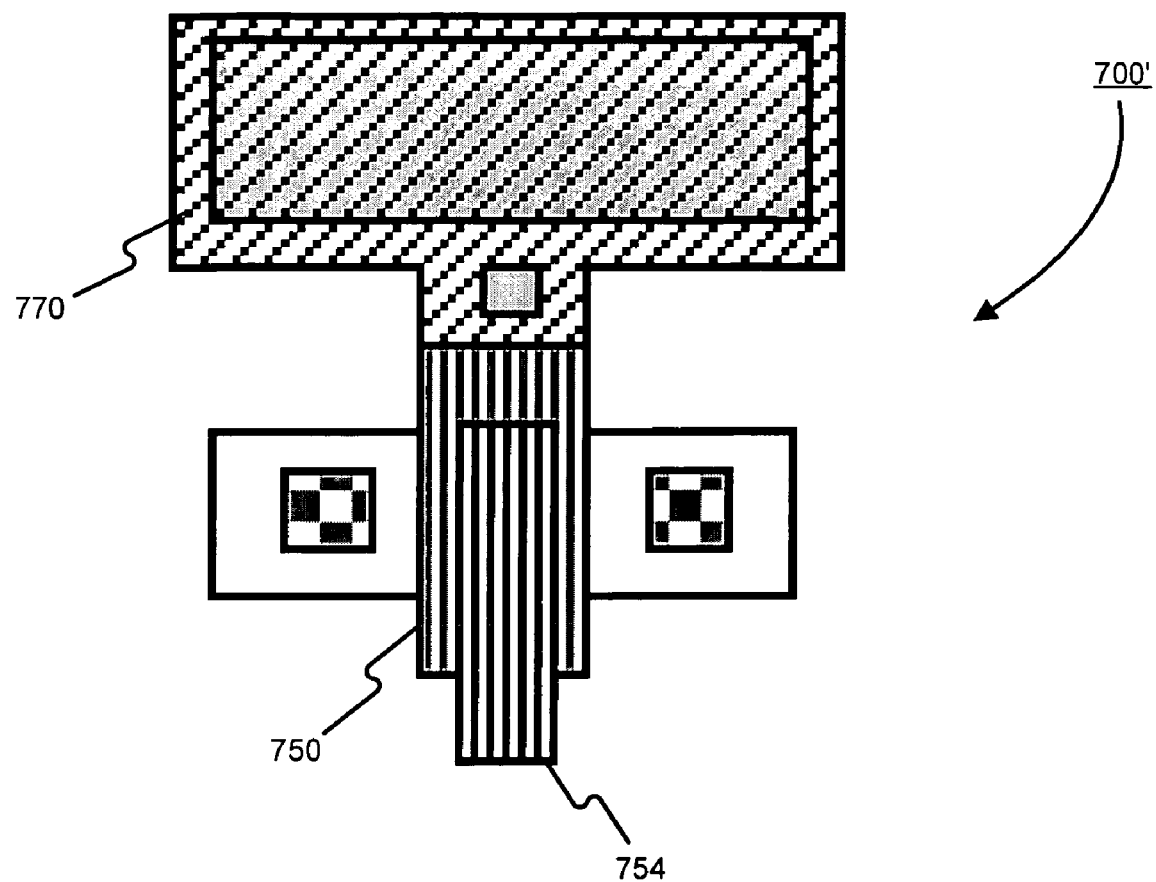

FIGS. 7A and 7B illustrates a cross sectional front view and plan view, respectively, of an exemplary floating gate ion sensitive field effect transistor that is consistent with the present invention. The FGISFET 700 is similar in operation to the FGISFETs described above, with reference to FIG. 3. In particular, the FGISFET 700 may comprise a substrate 710, an oxide layer 740, a source 720, a drain 730, a first floating gate 750, another oxide layer 752, a control gate 754, a dialectic (e.g., SiO2 insulator) 760, a first metal layer 762, another dielectric 764, a second metal layer 770, and a glass cover 780.

The FGISFET 700 may be fabricated using standard CMOS process—using a 2-polysilicon and 2-metal layer 1.2 μm process technology. Unlike conventional floating gate devices, used from EPROM or flash memory, the floating gate of an ISFET is electrically coupled with a receptor on a second metal layer 770. Generally, in 1.2 μm process technology, the second metal layer is encapsulated in glass, and the protective glass coating at chip periphery is etched to expose the bonding pads to create bond wire connections for packaging. In this design, the glass coating is also etched in selective locations to expose the second metal layer 770 receptors, connected to the floating gate 750. The exposed second metal layer 770 surface can be spin-coated with ion-sensitive materials for chemical and/or biological sensing.

Due to antenna effects, the floating gate 750 can collect positive or negative charges during plasma processing, and it might eventually create a high electric field within the gate oxide, leading to oxide breakdown. To avoid the consequences of antenna effects during fabrication, the floating gate 750 may be tied to the silicon substrate 710 ground terminal using a second metal layer 770 interconnect, thereby providing a discharge path for any accumulated charges on the floating gate 750. After the completion of all fabrication steps, the second metal layer 770 interconnect may be rendered non-functional (e.g., by cutting it with a focused laser beam), at which point the ISFET becomes functional. Instead of a single top gate, multiple top gates can be integrated to adjust the threshold voltage of ISFETs and improve their yield.

Figure 6:
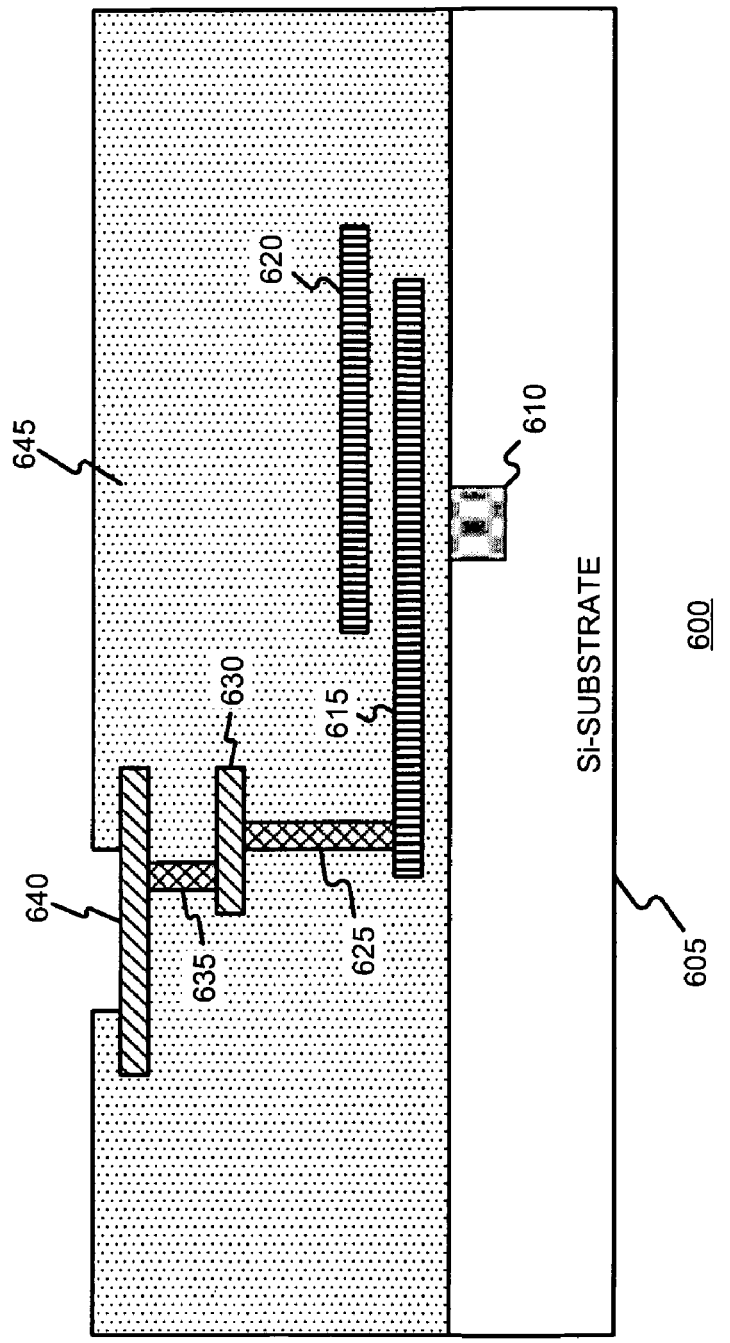
FIG. 6 illustrates a cross sectional side view of an exemplary floating gate ion sensitive field effect transistor that is consistent with the present invention.

FIG. 6 is a cross sectional side view which illustrates the electrical coupling of the floating gate 615 with a second metal layer 640, via a first conductor (e.g., wire) 625, first metal layer 630, and a second conductor (e.g., wire) 635. Also shown are glass 645, control gate 620, bulk substrate 605, and source (or drain) 610. As described above with reference to FIGS. 7A and 7B, sensing material (not shown) may be applied to the second metal layer.

§ 4.1.3 Method(s) of Use

Figure 8:
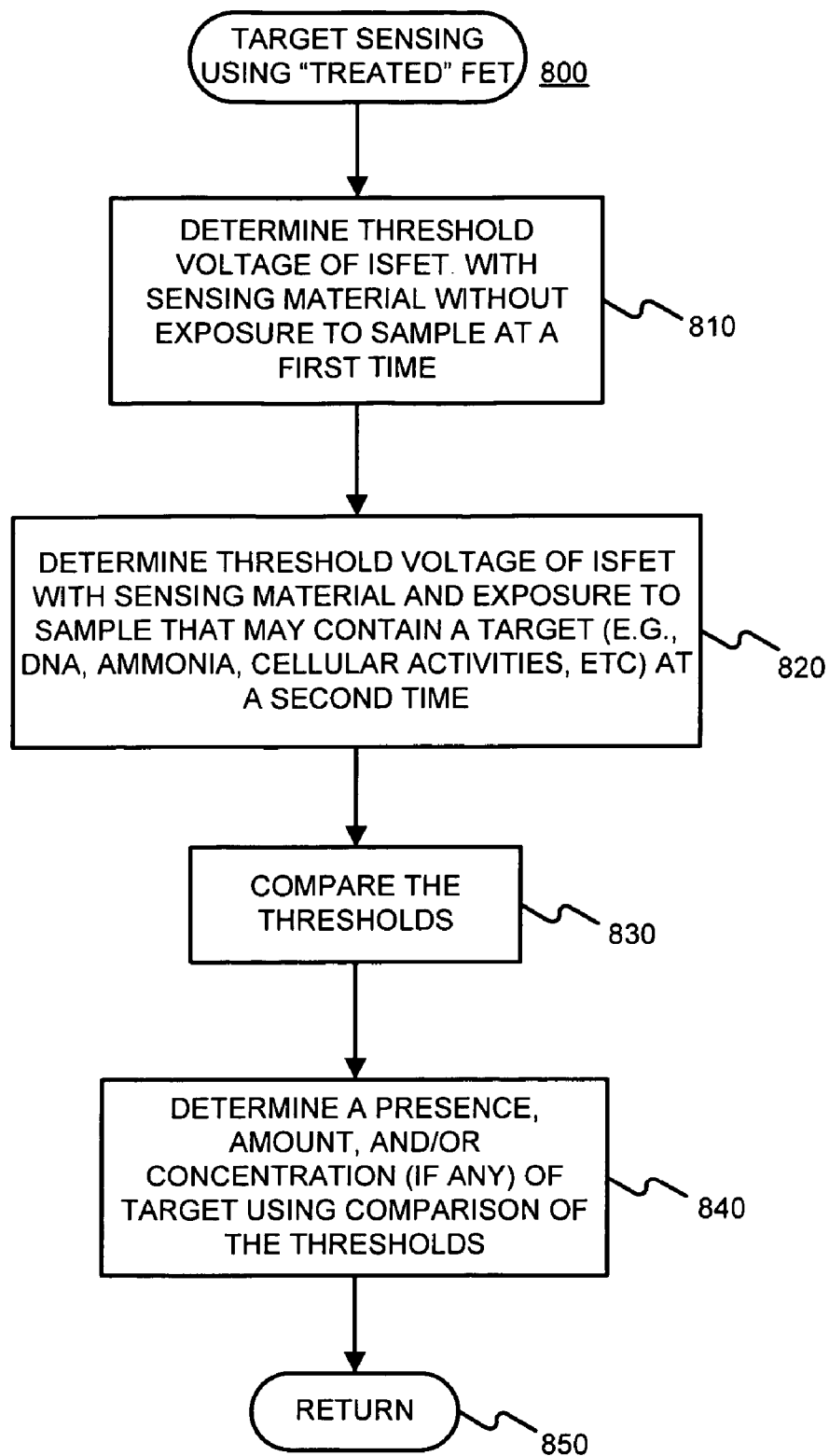
FIG. 8 is a flow diagram of an exemplary method that may be used to perform target sensing with an ISFET exposed to a sample, in a manner consistent with the present invention.

FIG. 8 is a flow diagram of an exemplary method 800 that may be used to perform target sensing with an FGISFET exposed to a sample, in a manner consistent with a first embodiment of the present invention. The threshold voltage of an FGISFET having sensing material is determined at a first time (before the FGISFET is exposed to a sample). (Block 810) Next, the FGISFET having sensing material is exposed to a sample that may contain a target material (e.g., gases (ammonia), chemicals, biological material (DNA, cellular activities), etc) and its threshold voltage is determined at a second time after such exposure. (Block 820) The two threshold voltages obtained by the same FGISFET are compared. (Block 830) For example, a threshold voltage shift may be discovered. Using this comparison (and perhaps other information) a presence, amount, and/or concentration of a target (if any) may be determined (Block 840) before the method 800 is left (Node 850).

Referring back to blocks 810 and 820, the threshold voltages may be determined using $\sqrt{I_{DS}}$ versus $V_{GS}$ plots, where the threshold voltage is simply located at the x-axis intercept, or determined using some other method. Using these plots shifts in threshold voltage may be determined.

Referring back to block 840, the voltage shift (if any), resulting from the ionic interactions between the sensing material (deposited on, or in electrical conduction with, the floating gate) and the sample, may be translated to material properties such as concentration, toxicity, amount, presence/absence, etc. For example, the voltage shift may be translated into a material property using a calibrated look-up table.

§ 4.2 SECOND EMBODIMENT

§ 4.2.1 Threshold Voltage Measuring Circuit

Figure 9:
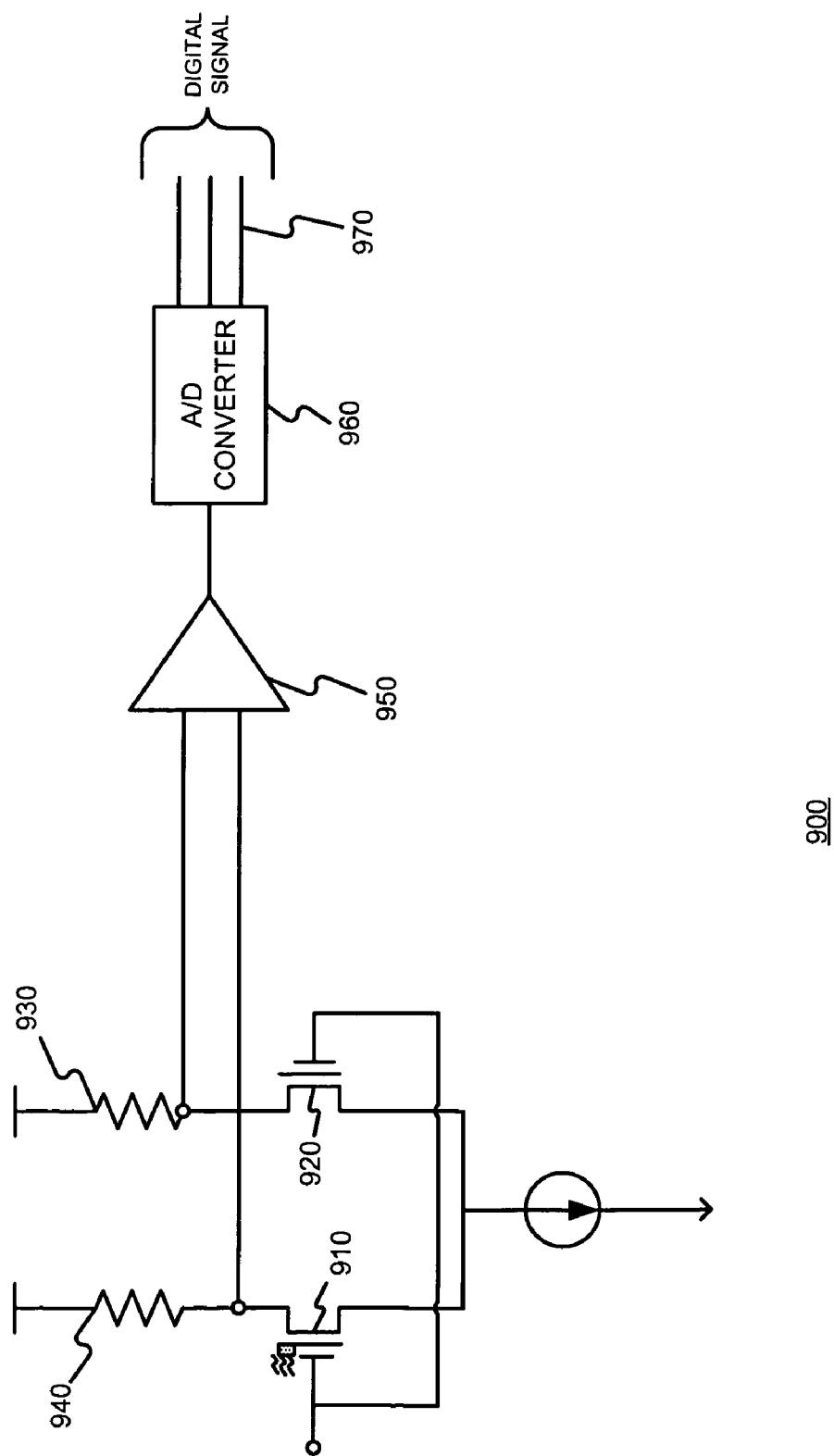
FIG. 9 illustrates an exemplary double ISFET sensor with a differential amplifier-based read-out circuit for generating a signal corresponding to voltage shifts (e.g., threshold voltage shifts) in a manner consistent with the present invention.

FIG. 9 illustrates an exemplary differential amplifier-based read-out circuit 900 for measuring threshold voltage shifts in a manner consistent with the present invention. The circuit 900 may include a differential amplifier 950 for outputting a voltage differential, an FGFET 910 with sensing material, an FGFET 920 without sensing material, resistors 930, 940 and an analog-to-digital converter 960.

The differential amplifier 950 can output a signal representing a threshold voltage difference between the two FGFETs 910 and 920. The amplified threshold voltage differential signal may be provided as an input to an analog-to-digital converter 960. Lines 970 may provide the digitized signal to a signal processing system (not shown) for translation of the signal to a target material property (e.g., presence, absence, amount, concentration, toxicity, etc.) measurement.

Figure 10:
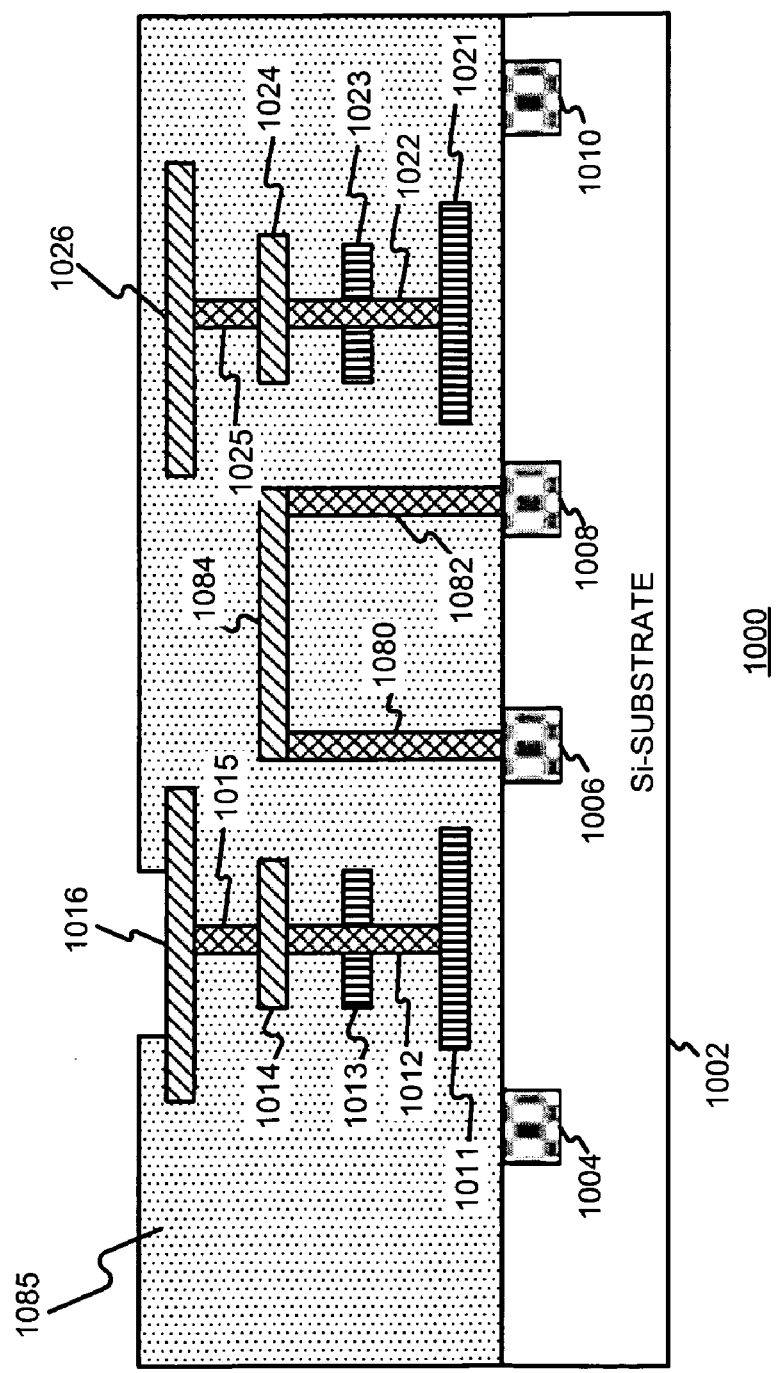
FIG. 10 illustrates a cross sectional side view of an exemplary double ISFET component, consistent with the present invention, which may be used in the exemplary double ISFET arrangement of FIG. 9.

FIG. 10 illustrates a cross sectional side view of an exemplary double ISFET component 1000, consistent with the present invention, which may be used in the exemplary circuit 900 of FIG. 9. The component 1000 may include a common or shared (e.g., Si) substrate 1002. The left FGFET is similar to that 600 described with reference to FIG. 6. The left FGFET may include a floating gate 1011, a source (or drain) 1006, a drain (or source) 1004, a control gate 1013, a first metal layer 1014 and a second metal layer 1016. A first conductor (wire) 1012 may electrically couple the floating gate 1011 with the first metal layer 1014, and a second conductor (wire) 1015 may electrically couple the first metal layer 1014 with the second metal layer 1016. The second metal layer 1016 may have a sensing material (not shown) on it, which may be exposed to the environment (e.g., not enclosed in glass 1085). The right FGFET may serve to provide a control (i.e., comparison) signal. The right FGFET may include a floating gate 1021, a source (or drain) 1008, a drain (or source) 1010, a control gate 1023, a first metal layer 1024 and a second metal layer 1026. A first conductor (wire) 1022 may electrically couple the floating gate 1021 with the first metal layer 1024, and a second conductor (wire) 1025 may electrically couple the first metal layer 1024 with the second metal layer 1026. The second metal layer 1026 may be isolated from the environment (e.g., enclosed by glass 1085), although this is not necessary. In some applications, it may be preferable to expose the second metal layer 1026 to the environment (e.g., not enclosed in glass 1085).

As shown, the sources (or drains) 1006 and 1008 may be electrically coupled (e.g., share a common terminal). In this regard, metal 1084 may be coupled with both 1006 and 1008 via conductors (e.g., wires) 1080 and 1082. Although not shown, the control gates 913 and 923 may also be electrically coupled, in which case the same biasing voltage source may be shared.

§ 4.2.2 Methods of Use

FIG. 11 is a flow diagram of an exemplary method 1100 that may be used to perform target sensing using a differential amplifier based read-out circuit, such as that shown in FIGS. 9 and 10 for example, in a manner consistent with the present invention. The threshold voltages of a first FGFET (without sensing material) and of a second FGFET (with sensing material) are obtained. (Blocks 1110 and 1120) Subsequently, the difference of the threshold voltages of the first and second FGFETs is determined. (Block 1130) The threshold voltage difference may be amplified by an amplifier and converted into a digital signal by an analog-to-digital converter. (Blocks 1140 and 1150) The (e.g., digital) signal may then be analyzed to determine a presence, amount, and/or concentration of a target (if any) (Block 1160), before the method 1100 is left (Node 1170).

Referring to blocks 1110, 1120, and 1130, a differential amplifier-based circuit, such as the one depicted in FIG. 9 for example, may be used to obtain the threshold values of the first and second FGFETs and determine the threshold voltage difference of the two FGFETs. Of course, other methods of obtaining threshold voltages are possible and may be used.

§ 4.3 EXPERIMENTAL RESULTS

Extensive measurements and characterization of a test chip have been performed to demonstrate key concepts of the FGISFET. These measurements indicate that it is feasible to coat the floating gate with sensing materials within a small (e.g., 200 µm×200 µm) region and their ionic properties are reflected by a shift in the device's threshold voltage. In one of the test cases, an aniline trimer has been used as the sensing material, which is a 3-benezene ring structure 1200 as shown in FIG. 12. At the Nitrogen (N) binding site, dopants can be incorporated to have specificity to a particular chemical, a particular class of chemicals, a specific biological material, or specific class of biological materials (e.g., pollutants, toxic chemicals, biological agents such as Bacillus anthracis, etc.). The aforementioned material 1200 was used as a sensing material to demonstrate the operation of such an FGISFET exposed to the target ammonia.

FIG. 13 is a chart depicting $\sqrt{I_{DS}}$ versus $V_{GS}$ characteristics of a FGISFET biased in saturation region, and indicating the initial threshold voltage of the FGISFET without the sensing material (aniline trimer). This chart depicts the initial characteristics of the floating gate ISFET without sensing material biased in saturation region. The x-axis intercept indicates the initial threshold voltage.

FIG. 14 is a chart depicting $\sqrt{I_{DS}}$ versus $V_{GS}$ characteristics of a FGISFET with an aniline trimer as a sensing material without exposure to the (70 ppm) ammonium target 1410, and the FGISFET with an aniline trimer as a sensing material exposed to the ammonium target 1420. FIG. 14 also shows the threshold voltages (about 4.2 V and 5.25 V). Again the x-axis intercepts indicate the threshold voltages. This chart depicts measurements of the same I-V characteristics as in FIG. 13.

FIGS. 13 and 14 illustrate preliminary experimental results of $V_T^{FG}$ shift when the floating gate of an nFET is coated with aniline trimer. Due to net negative charge concentration in the floating gate, there is a positive shift in $V_T^{FG}$. (Compare plot of FIG. 13 with plot 1410 of FIG. 14.) As the floating gate, coated with aniline trimer, is exposed to ammonia, there is an additional shift in device threshold voltage due to the de-doping of the sensing materials. (Compare plots 1410 and 1420.)

§ 4.4 EXTENSIONS AND REFINEMENTS

Embodiments consistent with the present invention can detect multiple targets, such as different types of gases and/or bacteria. Embodiments consistent with the present invention can reduce false alarms. In both cases, an array of FGISFETs may be used. A high-level block diagram of such FGISFET based system 1500, with a 4×4 array of ISFETs is illustrated in FIG. 15. Specifically, such a system 1500 may include a power management circuit (not shown), circuits for measuring threshold voltage shifts (and perhaps performing additional signal processing) 1510, a bias circuit 1540, an array of FGISFETs 1530, and lines 1520 for the application of row selection signals.

FIG. 16 illustrates a schematic diagram of an exemplary ISFET element 1630 consistent with the present invention, which may be used in an array such as the one depicted in FIG. 15. Line 1520a for application of row selection signal may be used to control switch 1632. A bias voltage $V_B$ is applied to the control gate of FGISFET 1634, which includes sensing material. Current flows from bias circuit (not shown) are also shown.

FIG. 17 illustrates a schematic diagram of exemplary shift measurement circuitry 1710, consistent with the present invention, which may be used in an array such as the one depicted in FIG. 15 and with an element 1630 such as the one depicted in FIG. 16. The circuitry 1710 includes an (e.g., matched) FGISFET 1712 without sensing material, differential amplifier 1714 and resistors 1716, 1718.

In at least some embodiments consistent with the present invention, the peripheral circuits of the FGISFET array may be similar to those of conventional static or dynamic memory, CMOS/CCC imagers, etc. For example, referring back to FIG. 15, in an array configuration, the $V_T^{FG}$ shift of all FGISFETs within the same row may be measured simultaneously by enabling their word line 1530. One by one all word lines 1530, one word line at any time, may be enabled and measurements of $V_T^{FG}$ shift for the entire array is completed. A calibrated look-up table can be used to convert the electrical signals to material properties such as concentration, toxicity, amount, presence/absence, etc. of the sensed target. During this phase, spatial correlation and advanced signal processing may be performed to improve the integrity of measured signals and to reduce false alarm rate.

Alternatively, or in addition, the use of integrated array of FGISFETs can be used to facilitate the detection of multiple targets simultaneously since different individual FGISFETs or different groups of FGISFETs can be made selective to different targets by applying appropriate sensing materials to their floating gates.

In addition to readout circuits, a power management unit can be integrated to switch off the power supplies when the FGISFET array is not in data acquisition mode. Such features are useful if the sensor array is to be deployed for environmental monitoring where it is desirable to conserve energy to extend battery life.

Various targets can be sensed by selecting the appropriate sensing material to be provided. For example, although experiments illustrating the operation of the present invention used aniline trimer to detect ammonium, various other sensing materials can be incorporated in FGISFET(s) to sense various other target materials. Generally, these sensing-target combinations display ionic behavior when the target binds (or otherwise interacts with, or comes into contact with) the sensing layer. For example, Table 1 lists potential sensing materials for use on FGISFET based applications.

TABLE I

| Sensing Material | Target | Application |
|---|---|---|
| Polyaniline | DNA | DNA Sensor |
| Aniline | Ammonia | Gas Sensor |
| Pheochromocytoma cells (PC12) | Cellular Activities | Cell-Base Sensor |

With appropriate synthesis, selection, and integration of sensing material, the FGISFET can be used to detect moisture, temperature, bacterium, DNA, protein, polymer, acids, gas or chemical solutions. Publicly available or proprietary techniques may be used for synthesis and integration of the sensing material. For example, covalent coupling may be use to immobilize the sensing material (also referred to as a "ligand") to the gate. Depending on the available reactive groups, amine, thiol and aldehyde coupling chemistries may be used. Immobilization techniques providing a more unidirectional ligand, such as streptavidin-biotin, may also be used. Different immobilization techniques are sometimes preferred for different types of ligands (such as acidic, base, or neutral peptides/proteins, nucleic acids, polysaccharides, of NH2, SH, COOH, CHO functional groups, etc.). U.S. (Utility and Provisional) patent application Ser. Nos.:

Ser. No. 10/170,903, titled "CHIRAL LIGAND EXCHANGE POTENTIOMETRY AND ENANTIOSELECTIVE SENSORS," filed on Jun. 13, 2002;

Ser. No. 10/242,590, titled "SURFACE IMPRINTING: INTEGRATION OF MOLECULAR RECOGNITION AND TRANSDUCTION," filed on Sep. 12, 2002;

Ser. No. 60/486,088, titled "BACTERIAL BIOSENSOR," filed on Jul. 10, 2003;

Ser. No. 10/888,342, titled "BIOSENSOR AND METHOD OF MAKING SAME," filed on Jul. 9, 2004;

Ser. No. 10/888,530, titled "BACTERIAL BIOSENSORS," filed on Jul. 9, 2004;

Ser. No. 10/719,688, titled "GLYCOCONJUGATE SENSORS," filed on Nov. 21, 2003; and Ser. No. 60/556,231, titled "IONIC BASED SENSING FOR IDENTIFYING GENOMIC SEQUENCE VARIATIONS AND DETECTING MISMATCH BASE PAIRS, SUCH AS SINGLE NUCLEOTIDE POLYMORPHISMS," filed on Mar. 25, 2004, describe immobilization techniques and/or sensing material-target material combinations that may be used. Each of these applications is incorporated herein by reference.

§ 4.5 CONCLUSIONS

In view of the foregoing, the present invention allows a reliable method for chemical and/or biological sensing using one or more floating gate ISFETs. At least some of these sensors can be minimized. At least some of these sensors can be used to detect charge changes (e.g., ion loss or gain) when a sensing material comes into contact with a target material. Such sensors have the potential to add tremendous value to our society, for example by aiding in the protection of our environment, cities, bridges, and tunnels from toxic gases or harmful biological agents.

What is claimed is:

1. A method for fabricating a floating gate field effect transistor, the method comprising:
   a) fabricating a floating gate field effect transistor using a 2-polysilicon and 2-metal layer 1.2 µm (or micron) process technology, wherein a floating gate is electrically coupled with a receptor on a second metal layer;
   b) encapsulating the second metal layer in glass;
   c) removing some of the glass to
      i) expose bonding pads on the second metal layer to create bond wire connections for packaging, and
      ii) expose at least a portion of the second metal layer; and
   d) immobilizing a ligand to the exposed portion of the second metal layer, wherein the act of immobilizing includes spin coating the exposed portion of the second metal layer with ion-sensitive material.

2. The method of claim 1 wherein the ion-sensitive material has a charge that changes in the presence of the target substance.

3. The method of claim 2 wherein the target substance is one of (A) a specific chemical and (B) a specific class of chemicals.

4. The method of claim 2 wherein the target substance is one of (A) a specific biological material and (B) a specific class of biological materials.

5. The method of claim 1 further comprising:
   e) electrically coupling the floating gate of the floating gate field effect transistor to a substrate of the floating gate field effect transistor, thereby providing a discharge path for any accumulated charges on the floating gate; and
   f) making the electrical coupling non-conducting after fabrication steps involving plasma.

6. The method of claim 1 further comprising:
   e) electrically coupling the floating gate of the floating gate field effect transistor to a substrate of the floating gate field effect transistor using a second metal layer interconnect; and
   f) making the second metal layer interconnect non-functional after fabrication steps of the 2-polysilicon and 2metal layer 1.2 µm (or micron) process technology involving plasma.

7. The method of claim 6 wherein the act of making the second metal layer interconnect non-functional includes cutting the second metal layer interconnect with a focused laser beam.

* * * * *